United States Patent [19]

Chandler

[11] Patent Number: 4,729,875
[45] Date of Patent: Mar. 8, 1988

[54] DEVICE FOR PERFORMING IMMUNOCHEMICAL ASSAYS

[75] Inventor: Howard M. Chandler, Orton, Canada

[73] Assignee: Allelix Inc., Mississauga, Canada

[21] Appl. No.: 880,948

[22] Filed: Jun. 26, 1986

[51] Int. Cl.⁴ .................. G01N 31/22; B01L 3/02; C12M 1/24

[52] U.S. Cl. .................... 422/58; 422/59; 422/60; 422/61; 422/69; 422/73; 422/100; 435/296; 436/807; 436/810

[58] Field of Search ............. 422/56, 61, 59, 60, 422/57, 58, 69, 100, 73; 435/296; 436/807, 810; 604/89, 90, 91, 191, 187, 220, 208, 210, 218; 222/135

[56] References Cited

U.S. PATENT DOCUMENTS

| | | | |
|---|---|---|---|
| 2,591,046 | 4/1952 | Brown | 604/90 |
| 3,807,119 | 4/1974 | Sheilds | 604/89 |
| 4,138,474 | 2/1979 | Updike | 422/101 |
| 4,178,803 | 12/1979 | Lee | 604/208 |
| 4,286,637 | 9/1981 | Wilson | 422/57 |
| 4,313,929 | 2/1982 | Morita et al. | 422/56 |
| 4,592,746 | 6/1986 | Burkholder et al. | 604/220 |

OTHER PUBLICATIONS

Chandler et al., "A New Enzyme Immunoassay System Suitable for Field Use & Its Appl. in a Snake Venom Det. Kit", Clin. Chim. Acta, 121(1982), pp. 225–230.

Primary Examiner—Michael S. Marcus
Assistant Examiner—Floyd E. Bennett, Jr.
Attorney, Agent, or Firm—Ridout & Maybee

[57] ABSTRACT

A device for performing a plurality of immunochemical assays simultaneously comprises a waste reservoir about which are positioned at least two assay tubes connected in series by conduits formed in the base and top of the reservoir structure. A compound syringe is insertable into an opening formed through the top of the waste reservoir, the syringe being held in place by a receiving structure formed in the base of the reservoir and connected to the entrance end of the series of assay tubes. The various compartments of the compound syringe are emptied in sequence to cause the flow of sample and assay reagents to flow through the assay tubes. The device is structured to allow for the reflow of sample through the tubes if desired.

11 Claims, 8 Drawing Figures

DEVICE FOR PERFORMING IMMUNOCHEMICAL ASSAYS

The present invention relates to a device for performing immunoassays. The device is especially suitable for qualitative assays and may be adapted for quantitative determinations.

The invention provides a device for performing an assay quickly and accurately using an inexpensive, disposable apparatus. The assay may be accomplished on a relatively small fluid sample, and requires only small amounts of expensive reagents. The device takes advantage of recent developments in immunology pertaining to the production of tailor-made monoclonal antibodies.

The need to provide rapid and accurate assays is well recognized in the medical field, but also is important and highly desirable in environmental, agricultural and industrial situations. In these latter areas it is often highly desirable to obtain a quick determination of the presence of a specific substance in a water, soil, product or effluent sample. Enzyme immunochemial assays are finding increasing applications in these latter areas, and the need to provide a portable, reliable and easy to use device for this purpose is clear.

The device of the invention satisfies these needs by enabling the user to perform one or a plurality of immunoassays simultaneously on a single sample. The device accomplishes this multiple use by being able to accommodate a plurality of assay tubes, each tube being coated on the inner wall thereof with, for example, a different monoclonal antibody. The assay tubes are arranged in series so that a single sample may be flowed through each tube. The device contains its own waste reservoir so that no mess is involved in performing the assay.

In an antibody sandwich type of assay, the sample being tested is mixed with one or more monoclonal antibodies each conjugated to an enzyme. The monoclonal antibodies used for the antibody/enzyme conjugates are, generally, different from the monoclonal antibodies affixed in the assay tubes. The sample is then contacted with antibodies fixed to the walls of the tubes and any captured material is detected by introducing enzyme substrate into the tubes, the conversion of which by the enzyme is detected by, for example, a change in the pH or optical density of the solution in a tube.

The present device may be adapted to carry out any of the commonly used enzyme immunoassays to detect antigen, hapten or antibody. The device importantly has the capability of performing a plurality of assays at the same time so that, for example, a blood sample may be screened for a series of infectious diseases quickly and accurately using the invention.

Accordingly, the present invention provides a device for performing immunochemical assays, comprising at least two transparent tubes connected in series with at least one of the tubes having an antigen, hapten or antibody attached to the internal surface thereof. A syringe is connectable to one end of the connected tubes, and a hollow plunger is insertable into the syringe for forcing liquid therefrom into the tubes. The hollow plunger is provided with structure at one end defining an exit opening, the structure being insertable into the exit opening of the syringe. The plunger has first and second pistons positioned within it defining first and second chambers. Each piston has first and second spaced circumferential surfaces for engaging the inner wall of the plunger thereby defining an annular space about each piston. The inner wall of the plunger has first and second grooves for receiving the circumferential surfaces of the first piston when it has been moved near the exit structure. The grooves, piston and inner wall define a fluid pathway from the second chamber to the plunger exit. A separate plunger is provided for depressing the pistons in the hollow plunger, and a waste reservoir is connected to the exit end of the tubes, the connection providing access for the tubes to the fluid deposited therein.

This latter feature allows the test sample to be reflowed or back flowed through the tubes into the syringe by merely drawing back on the hollow plunger. The ability to provide reflow of the sample is important for increasing the sensitivity of the assay, especially when the assay is being conducted on a relatively small sample. A preferred embodiment of the invention will be described with reference being made to the drawings in which.

Figure 1:
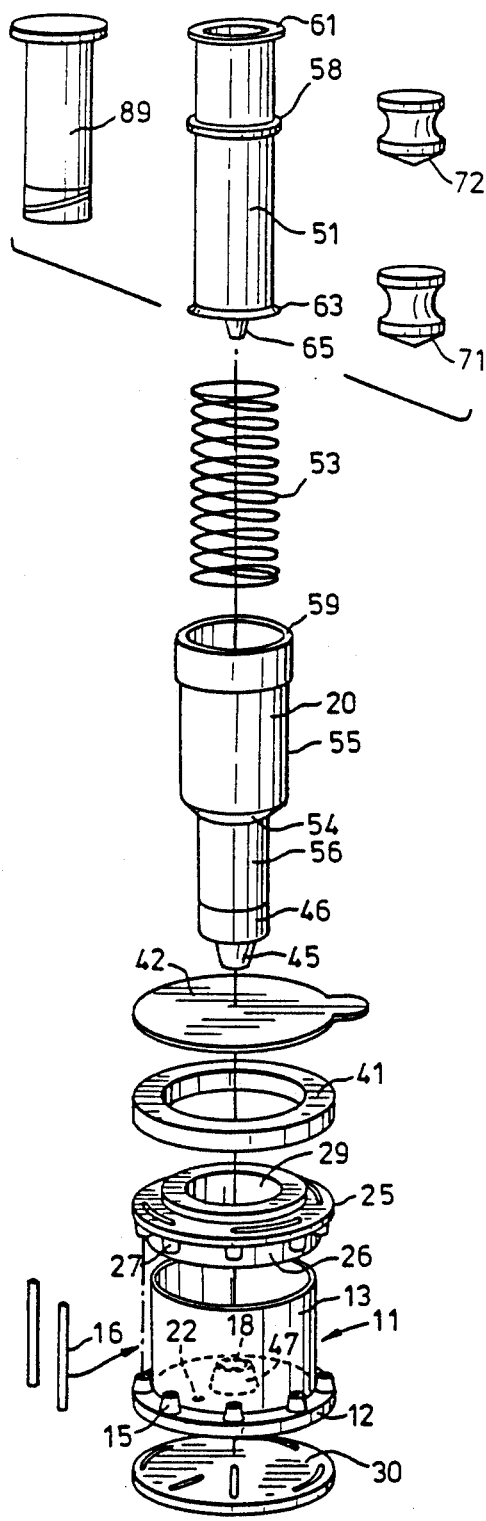
FIG. 1 is an exploded view of a device in accordance with the invention.
Figure 2:
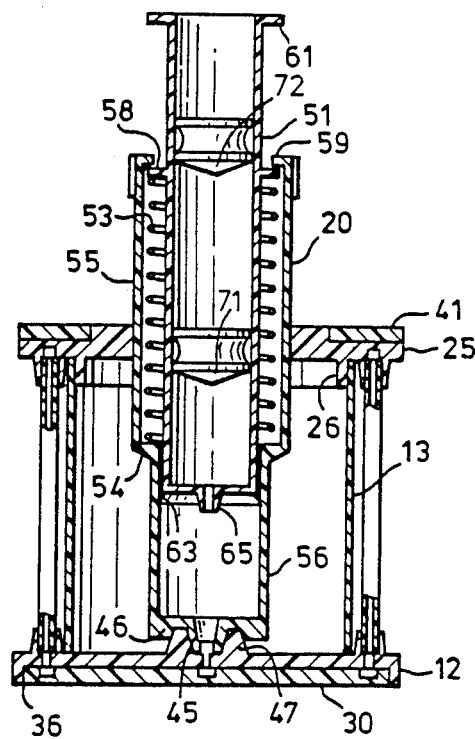
FIG. 2 is a cross sectional view of an assembled device.
Figure 7:
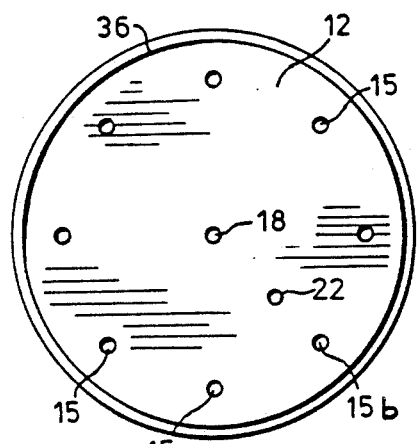
FIG. 7 is a plan view of the underside of the waste reservoir.
Figure 8:
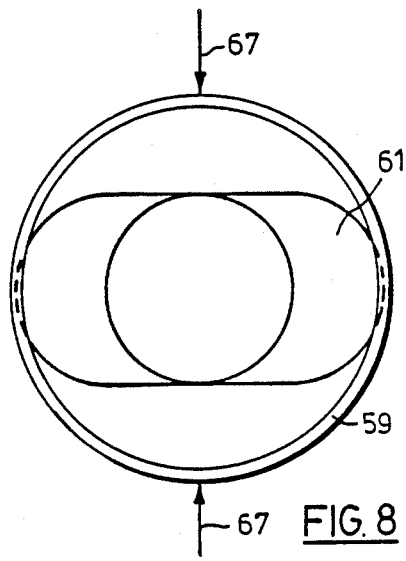

FIG. 8 is a top plan view of the hollow plunger locked in the syringe. Referring to FIGS. 1 and 2, the preferred device according to the invention comprises a waste reservoir 11 having a bottom 12 and upright sidewall 13 which preferably are circular and cylindrical respectively. The bottom 12 extends outward beyond the sidewall 13 and is provided with a plurality of openings 15 near the periphery thereof into which transparent assay tubes 16 are insertable. The device requires at least two such assay tubes 16 connected in series as will be described below. The bottom 12 is also provided with an opening 18 (see FIG. 7) within the reservoir 11 for receiving an end of a syringe 20, and an opening 22 for depositing fluid in the reservoir 11 from the syringe 20 and tubes 16.

The reservoir 11 has a top member 25 with a downwardly extending flange 26 which snugly engages the sidewall 13. The top member extends outwardly beyond the sidewall 13 and has a plurality of openings 27 near the periphery thereof registrable with the openings 15 in the bottom 12 into which the tubes 16 may be inserted. The top member 25 has an opening 29 for receiving the syringe 20. The opening 29 is located to enable the insertion of the end of the syringe 20 into the opening 18 in the bottom 12.

Figure 6:
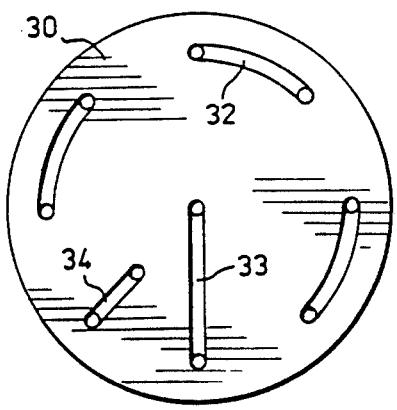
FIG. 6 is a plan view of the bottom member showing conduits for connecting the assay tubes to one another and to the syringe and waste reservoir.

Circuitry is provided in the bottom 12 and top 25 to allow fluid to flow from the syringe 20, through the tubes 16 in series and finally, into the reservoir 11. Circuitry for the bottom 12 is provided in a base plate 30 (see FIG. 6) having grooves 32 therein for connecting pairs of tubes 16, a groove 33 from the syringe 20 to the first tube 16, and a groove 34 from the last tube 16 to the reservoir 11. The base plate 30 is affixed to the bottom 12 within a downwardly depending flange 36 of the bottom 12. Clearly, the opening 18 and an opening 15a in the bottom 12 are oriented in register with the groove 33, as is the groove 34 with the opening 22 and an opening 15b as shown in FIGS. 6 and 7.

Likewise, the top 25 is provided with grooves 38 for connecting adjacent pairs of tubes 16. The top 25 is oriented so that the grooves 38 alternate with the grooves 32 in the base plate 30 thereby effecting a series circuit for the tubes 16. As shown, the grooves 38 are provided in the top surface of the top 25 so an annular member 41 is affixed thereover to create the necessary conduits.

The reservoir 11, base plate 30, top 25 and annular member 41 may be assembled with at least two tubes 16 and up to any even number of tubes 16 which the dimensions of the components will permit. When only two tubes 16 are used, they must be inserted in openings 15a and 15b in the bottom 12 of the reservoir 11 and clearly, grooves 32 are not needed in the base plate 30. Likewise, only one groove 38 is needed in the top 25 for the purpose of connecting the upper ends of the two tubes 16.

For packaging and shipping purposes, a lid 42 is preferably provided over the annular member 41 to seal the device prior to use (see FIG. 1). The lid 42 may be adhered to the member 41 with any suitable peelable adhesive readily available on the market.

From the foregoing it should be appreciated that the device is capable of performing a plurality of enzyme immunoassays simultaneously by employing a plurality of assay tubes 16 arrayed about the reservoir 11 and connected together in series. Each assay tube 16 may have a different antibody, antigen or hapten attached to its inner surface for the purpose of providing separate assays on the same sample. As will become clearer from the description which follows, the device preferably uses monoclonal antibodies to carry out the assays since these reagents enable the assays to be carried out in fewer steps and hence, tend to give quicker results than is the case with serum antibodies.

The sample for testing as well as the reagents needed to carry out the assays are caused to flow through the assay tubes 16 and into the waste reservoir 11 by means of a compound syringe 20. As shown in FIG. 2, the syringe 20 has structure at one end defining a fluid passageway 45 and a circumferential end flange 46 which may coact with a syringe receiving structure 47 provided about the opening 18 in the bottom 12 of the reservoir 11. The syringe passageway 45 and flange 46 preferably snap fit with the structure 47 to provide a secure seating of the syringe in the reservoir 11.

The syringe 20 has a hollow plunger 51 which is itself a syringe. As shown in FIGS. 1 and 2, the plunger 51 coacts with a spring 53 which biases the plunger 51 toward the retracted position. The spring 53 is coiled about the plunger 51, the lower end of the spring 53 engaging a stepped portion 54 of the syringe 20 which separates the syringe into an upper portion 55 and a lower portion 56. The upper end of the spring 53 engages a flange 58 located toward the upper end of the plunger 51. This flange 58 is also engagable with an inwardly extending flange 59 about the top of the upper portion 55 of the syringe 20. This flange 58 serves to restrain the retracting movement of the plunger 51 under the influence of the force from the spring 53. The flanges 58 and 59 are preferably circular and thus, preferably extend fully about the circumference of both the plunger 51 and the syringe 20. Additionally, a flange 61 is preferably provided at the top end of the plunger 51. As shown in FIG. 8, this flange 61 is preferably circularly oblong shaped with only the opposing rounded portions being engagable with the circular flange 59 of the syringe 20.

The lower end of the plunger 51 has a circumferential lip 63 which engages the inner surface of the lower portion 56 of the syringe 20 when the plunger 51 is inserted therein. The lower portion 56 of the syringe 20 defines a chamber for the test sample. The lip 63 on the plunger 51 enables a clean expulsion of fluid sample from the lower portion 56 of the syringe 20. The lower end of the plunger 51 has an exit structure 65 defining passageway for fluids within the hollow plunger 51 to be expelled therefrom. The exit structure 65 is insertable into the fluid passageway 45 of the syringe 20, and the relative dimensions of the syringe 20 and plunger 51 are designed so that the exit structure 65 is so inserted in the passageway 45 when the top flange 61 of the plunger 51 is engaged with the top flange 59 of the syringe 20.

The syringe 20 and hollow plunger 51 are preferably made of a plastic material having a degree of resilience. For the purpose of drawing a test sample into the lower portion 56 of the syringe 20, the syringe 20 is taken with the plunger 51 locked down by the interengaging flanges 59 and 61 and the lower end thereof is inserted into the test fluid. Finger pressure is applied about the flange 59 at the top of the syringe 20 at the flange 59 portions not engaging the plunger flange 61 (see arrows 67, FIG. 8). This pressure causes the flange 59 to deform sufficiently to release the flange 61 and hence, the plunger 51. The spring 53 forces the plunger 51 to retract thereby drawing test fluid into the chamber of the lower syringe portion 56. Clearly, the circular flange 58 on the plunger 51 is positioned relative to the top flange 61 to create the desired chamber volume in the lower portion 56 of the syringe 20. After drawing the test sample into the syringe 20, the syringe 20 is inserted through the top opening 29 in the reservoir 11 and the passageway structure 45 and flange 46 are snap fit with the receiving structure 47.

At this point an important feature of the invention may be understood. The sample may be expelled from the syringe 20 by depressing the plunger 51. The sample flows through the conduit provided by the groove 33 in the base plate 30, through the assay tubes 16 connected in series and finally into the waste reservoir via the conduit provided by the groove 34 in the base 30. Because the bottom 12 of the reservoir 11 is at about the level of the lower ends of the tubes 16, fluid contact is maintained through the circuitry from the syringe 20 to the reservoir 11. Thus, release of the plunger 51 allows it to retract under the force of the spring 53 to cause the sample to be drawn back into the syringe 20 from the reservoir 11 via the assay tubes 16. The sample may be recirculated in this way through the assay tubes 16 for as long as needed to meet the sensitivity requirements of the various assays being performed.

It will be appreciated that the sensitivity of an assay is generally increased by contacting the sample with the antibody, antigen or hapten fixed to the inner wall of an assay tube 16 for sufficient time to enable a detectable amount of substance being assayed for to be captured by the antibody, antigen or hapten so fixed. Because the antibody, antigen or hapten is fixed at the wall of the tube 16, the rate of capture of the assayed substance is dependent on its concentration at the tube wall. By flowing the test sample along the tube wall, the concentration of assayed substance is constantly being renewed, hence the rate of capture at the tube wall is greatly increased as compared to a static situation. By having the ability to reflow or recirculate the sample through the assay tubes 16, the required sensitivity may be obtained in the optimum time using a relatively small sample volume. Clearly, the structure of the present device enables the achievement of these desirable and useful results.

Figure 3:
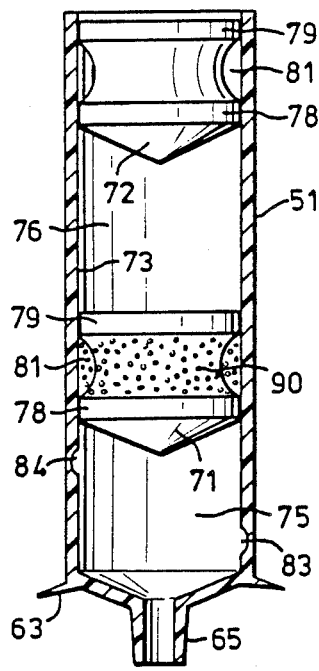
FIG. 3 is a sectional detail of the hollow plunger in the loaded configuration.
Figure 4:
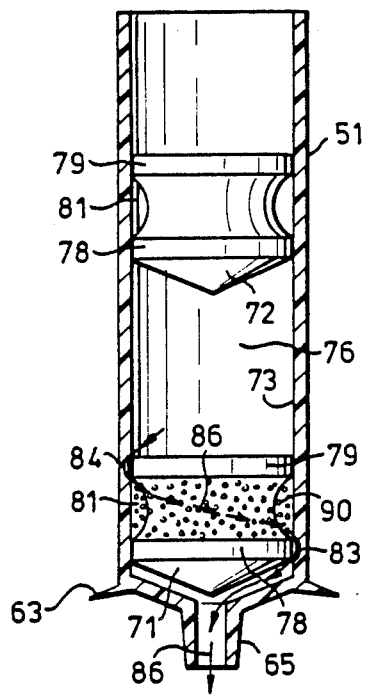
FIG. 4 is the same view as FIG. 3 showing the plunger with the first piston depressed.
Figure 5:
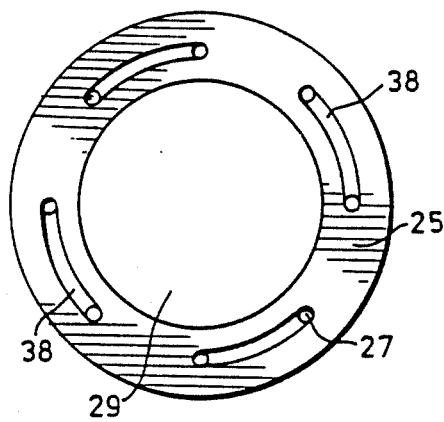
FIG. 5 is a plan view of the top member showing conduits for connecting the assay tubes.

Referring finally to the structure of the hollow plunger 51 as shown in detail in FIGS. 3 and 4, it can be seen that the plunger 51 also functions as a syringe. The plunger 51 has a first piston 71 and a second piston 72. The pistons 71 and 72 are not attached to a plunger, and are spaced from one another to define with the inner surface 73 of the plunger 51 a first chamber 75 and a second chamber 76. The pistons 71 and 72 each have first and second circumferential surfaces 78 and 79 for engaging the inner wall 73 of the plunger 51 defining an annular space 81 between the pistons 71 and 72 and the wall 73. This structure is only needed for the lower or first piston 71, but for ease of assembly, both pistons 71 and 72 are preferred to be of this shape.

The wall 73 of the plunger 51 has first and second grooves 83 and 84 therein for receiving the first and second circumferential surfaces 78 and 79 of the first piston 71 when the piston 71 has been moved near the exit structure 65 of the plunger 51. The grooves 83 and 84, annular space 81, piston 71 and wall 73 define a fluid pathway (arrows 86) from the second chamber 76 to the exit structure 65. In other words, the grooves 83 and 84 both restrain the piston 71 from sealing engagement about the exit structure 65 and provide a pathway for fluid to flow from the second chamber 76 past the piston 71 and out through the exit structure 65.

As shown in FIG. 4, the grooves 83 and 84 are arranged diagonally opposite one another to provide a pathway 86 which encourages fluid flow through most of the annular space 81. This feature allows for the inclusion of a powdered, solid reagent 90 in the annular space 81 about the first piston 71 which is dissolved in the liquid flowing through the fluid pathway 86. Since reagents are generally less stable in solution, the ability to provide active reagents in powder or solid form until just before they are required in solution for performing the assays increases significantly the shelf life of the assay device.

This feature alone may determine the difference between a commercially viable and non-commercial assay device.

As shown in FIG. 1, the device includes an unattached plunger 89 for depressing the pistons 71 and 72 in the hollow plunger 51. Since both plunger chambers 75 and 76 are initially charged with liquids, downward pressure exerted on the second piston 72 by the plunger 89 is hydraulically transmitted to the piston 71 so that both pistons 71 and 72 move down the hollow plunger 51 in unison until the first piston engages the grooves 83 and 84. The opening of the pathway 86 allows the second piston 72 to continue down the plunger 51 to engagement with the piston 71 thereby expelling the contents of the second chamber 76 through the exit structure 65.

Having described the structural features of the preferred embodiment of the invention, a more complete understanding of how the structure functions to perform enzyme immunochemical assays may obtained by reference to the following example.

A commonly performed enzyme immunoassay is a test for pregnancy in humans wherein the presence of human chorionic gonadotropin (HCG) is assayed for in urine. The present assay device is provided with two tubes 16 both of which are transparent and one of which has HCG antibody (anti-HCG) attached, preferably by covalent bonding, to the inner wall thereof. The other tube may serve as a reference blank. The anti-HCG attached to the inner wall of the assay tube 16 is a monoclonal antibody, that is, it is specific to a particular antigenic site on HCG.

A urine sample to be tested is mixed with HCG antibody/enzyme conjugate wherein the HCG antibody is a monoclonal antibody specific to a different antigenic site on HCG than is the case for the anti-HCG used in the assay tube 16. The enzyme is preferably urease. The antibody and enzyme are bonded together to form the antibody/enzyme conjugate in a manner well known in this art. Conveniently, the antibody/enzyme conjugate may be provided within the lower portion 56 of the syringe 20 so that only sufficient conjugate need be supplied to react with the actual test sample used. This, of course, minimizes the cost of reagents and eliminates the need to perform a step on the sample prior to introduction into the syringe 20. The enzyme conjugate may be conveniently provided in the lower portion 56 of the syringe 20 by impregnating a solid substrate with the conjugate and inserting the substrate into the lower portion 56 upon assembly of the syringe 20 and plunger 51. A preferred arrangement in this regard is to provide the enzyme conjugate in a foamed plastic substrate which is affixed about the exit structure 65 of the plunger 51. The enzyme conjugate is in a stable solid form in accordance with this embodiment and is quickly dissolved in the test sample when it is drawn into the syringe 20.

A urine sample is drawn into the lower syringe portion 56 as previously described, and often preferably allowing an incubation period for the enzyme conjugate to react with HCG present therein, the sample is forced through the tubes 16 and into the reservoir 11 by depressing the plunger 51. Of course, the enzyme conjugate will continue to react with any HCG present in the sample during this stage of the assay. The sample is reflowed back and forth through the tubes 16 by releasing and depressing the plunger 51 for 1–3 minutes.

The plunger 51 is then pushed firmly down to engage the exit structure 65 within the fluid passageway 45 of the syringe 20. This configuration is maintained by causing the top circularly oblong flange 61 to be captured beneath the circular flange 59 of the syringe 20. The plunger 89 is then used to depress the second or top piston 72 of the hollow plunger 51 which causes a wash solution in the lower chamber 75 of the hollow plunger 51 to be expelled through the fluid passageway 45, the tubes 16 and into the reservoir 11.

At this stage in the assay, any detectable amount of HCG in the urine sample should be captured at the inner wall of the assay tube 16 as an enzyme conjugate/HCG/antibody sandwich. Detection of the captured HCG may then be effected by providing substrate for the enzyme, the consumption of which may be detected by, for example, a change in pH. In the present example, urea is the substrate for the urease of the enzyme conjugate, and a metabolic product of urea consumption by the urease is ammonia which causes an increase in the pH of the aqueous solution in the assay tube 16. The pH rise may be detected by a color forming indicator such as bromthymol blue.

Because urea is not stable for more than a few days when in solution, powered urea is provided in the annular space 81 of the lower piston 71 of the hollow plunger 51. The powdered urea is indicated as reference numeral 90 in FIGS. 3 and 4. Alternatively, the urea may be impregnated in a solid substrate which is positioned in the annular space 81. For example, filter paper may be soaked in a urea containing solution and then dried, a strip of such impregnated paper then being provided in the annular space 81.

The liquid in the upper or second chamber 76 is a suitable aqueous solute for the urea also containing the pH indicator. Continued pressure on the piston 72 by the plunger 89 causes the solute in the chamber 76 to flow through the fluid pathway 86 dissolving the urea in the annular space 81. The solution then continues through the tubes 16 flushing out the wash liquid. Because of the fluid continuity of the circuitry of the device, the assay tube 16 remains filled with substrate solution so that the enzymatic conversion of the urea can take place. A positive assay result will be shown by a color change in the assay tube within an incubation period of no more than 10 minutes.

I claim:

1. A device for performing immunochemical chemical assays, comprising:
    at least two transparent tubes, each having an internal surface, said tubes being disposed side by side and connected in series, thereby defining a first end and a second end for the connected tubes, at least one of the tubes having an antigen, hapten or antibody attached to the internal suface thereof;
    a syringe having a fluid passageway defined at one end thereof, and having a tubular body defining a chamber capable of receiving a fluid test sample;
    means for connecting the syringe to the first end of said connected tubes, so that the syringe chamber may be in fluid communication with said connected tubes through said fluid passageway;
    and a hollow plulnger insertable into the syringe for forcing liquid therefrom into the connected tubes, the plunger having an inner wall and an exit structure which is insertable into the fluid passageway of the syringe, the hollow plunger having first and second pistons positioned within it, a first plunger chamber being defined between the first piston and said exit structure, and a second plunger chamber being defined between the first and second pistons, the first piston having first and second spaced circumferential surfaces for engaging the inner wall of the plunger thereby defining an annular space between the first piston and the inner wall of the plunger, the inner wall of the plunger having first and second means for coacting with the first and second circumferential surfaces of the first piston when said first piston has been moved near the exit structure, said first and second means, said first piston and said inner wall of the plunger defining a fluid pathway including said annular space from the second plunger chamber to the exit structure;
    means for depressing the first and second pistons of the hollow plunger; and
    a waste reservoir connected to the second end of the connected tubes, the connection providing access for the tubes to fluid deposited therein so that said fluid may be back flowed through the tubes by means of suction from the syringe, the waste reservoir comprising a base member, an upright side wall and a top member; the base and top members having portions extending outwardly from the sidewall and having openings therein for receiving each of the at least two tubes, the base member having openings in flow communication with the reservoir for receiving the end of the syringe and for depositing fluid into the reservoir; conduit means in the base member connecting said openings to the first and second ends of said connected tubes, and conduit means in the base and top members for connecting the tubes in series; and the top member defining an opening therein for receiving the syringe.

2. A device as claimed in claim 1, further oomprising means positioned within the syringe chamber for providing therein at least one enzyme conjugate.

3. A device as claimed in claim 1, wherein the annular space about the first piston contains an enzyme substrate in solid form, the first plunger chamber contains a wash solution, and the second plunger chamber contains a solute for the enzyle substrate.

4. A device as claimed in claim 1, wherein the means for depressing the pistons in the plunger is a rod.

5. A device as claimed in claim 1, wherein the top member contains grooves between alternating adjacent openings in the top member, said grooves being formed in an upper surface of the top member, said device further including a cover member positioned and arranged over the top member grooves to form said conduit means.

6. A device as claimed in claim 1, wherein each of the at least two tubes extends from the base member to the top member at the portions thereof which extend beyond the upright sidewall of the waste reservoir, said tubes being connected in series by means of the conduit means formed in the base and top members, the conduit means in the base being provided by a base plate attached to the bottom of the base member, the base plate having grooves therein so that the base plate and base member coact to form the conduit means in the base, and the conduit means in the top member being provided by grooves formed between alternating adjacent openings formed through the top member to receive the tubes, said grooves being formed in an upper surface of the top member, and a cover member being affixed over the top member and the grooves to form the conduit means.

7. A device as claimed in claim 1, further comprising a base plate attached to a bottom of the base member, the base plate having grooves therein so that the base plate and base member coact to form the conduit means.

8. A device as claimed in claim 1, wherein the first and second means for coacting with the first and second circumferential surfaces of the first piston are first and second grooves formed in the inner wall of the plunger.

9. A device as claimed in claim 1, wherein said means for connecting the syringe to the first end of the connected tubes comprises a receiving structure in the bottom member which coacts with the end of the syringe defining the fluid passageway so that the passageway is held in fluid communication with said first end of the connected tubes.

10. A device as claimed in claim 1, further comprising a spring coacting with the plunger to bias the plunger toward a retracted position, and interegagable flanges on the syringe and plunger which provide a restriction to the extent of plunger retraction.

11. A device as claimed in claim 10, wherein the flanges on the syringe and plunger are circular, and the plunger also has a circular oblong shaped flange spaced from said circular flange on the plunger, the circular oblong flange being proportioned to engage the circular flange of the syringe to lock the plunger in a depressed position so that the exit structure thereof is inserted into the fluid passageway of the syringe.

* * * * *